United States Patent
Prasad

(10) Patent No.: US 8,546,087 B2
(45) Date of Patent: Oct. 1, 2013

(54) DIAGNOSIS OF RESTENOSIS IN PATIENTS UNDERGOING PERCUTANEOUS CORONARY INTERVENTION

(75) Inventor: Kailash Prasad, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 13/375,924

(22) PCT Filed: Jun. 2, 2010

(86) PCT No.: PCT/CA2010/000833
§ 371 (c)(1),
(2), (4) Date: Jan. 26, 2012

(87) PCT Pub. No.: WO2010/139063
PCT Pub. Date: Dec. 9, 2010

(65) Prior Publication Data
US 2012/0128660 A1    May 24, 2012

Related U.S. Application Data

(60) Provisional application No. 61/183,613, filed on Jun. 3, 2009.

(51) Int. Cl.
*G01N 33/68* (2006.01)
*C07K 14/435* (2006.01)

(52) U.S. Cl.
USPC .............................. 435/7.1; 530/350; 530/830

(58) Field of Classification Search
None
See application file for complete search history.

(56) References Cited

PUBLICATIONS

International Search Report and Written Opinion issued Aug. 24, 2010 in PCT/CA2010/000833.
Written Opinion issued Aug. 17, 2011 in PCT/CA2010/000833.
Response to First Written Opinion filed Mar. 24, 2011 in PCT/CA2010/000833.
Response to Second Written Opinion filed Sep. 15, 2011 in PCT/CA2010/000833.
IPRP issued Oct. 7, 2011 in PCT/CA2010/000833.
Empana et al., Contribution of novel biomarkers to incident stable angina and acute cornoary syndrome: the PRIME study, European Heart Journal, 29:1966-1974, 2008.
Braquet et al., Role of Cytokines and Platelet-Activating Factor in Microvascular Immune Injury. Int Arch Allergy Appl Immunol. 1989;88(1-2):88-100.
Chavakis et al., The Pattern Recognition Receptor (RAGE) is a Counterreceptor for Inflammatory Cell Recruitment. J. Exp. Med. Nov. 17, 2003;198(10):1507-1515.
Chiu et al., Reactive Oxygen Species are involved in Shear Stress-Induced Intercellular Adhesion Molecule-1 Expression in Endothelial Cells. Arterioscler Thromb Vasc Biol. Dec. 1997;17(12):3570-3577.
Devaraj et al., The Effects of Alpha Tocopherol Supplementation on Monocyte Function. J. Clin. Invest. Aug. 1, 1996;98(3)156-763.
Falcone et al.,Plasma Levels of Soluble Receptor for Advanced Glycation End Products and Coronary Artery Disease in Nondiabetic Men. Arterioscler Thromb Vasc Biol. May 2005;25(5):1032-1037.

(Continued)

*Primary Examiner* — Zachary Howard
(74) *Attorney, Agent, or Firm* — Michael A. Wittaker; Acuity Law Group, P.C.

(57) ABSTRACT

The present invention relates to compounds, compositions, methods and/or kits for determining and/or predicting and/or diagnosing and/or treating restenosis in a patient.

14 Claims, 13 Drawing Sheets sRAGE, sVCAM-1, TNF-α and AGE in Control and NSTEMI Subjects

(56) References Cited

PUBLICATIONS

Faruqi et al., Alpha-Tocopherol Inhibits Agonist-induced Monocytic Cell Adhesion to Cultures Human Endothelial Cells. J. Clin. Invest. Aug. 1994;94(2):592-600.
Gearing and Newman, Circulating adhesion molecules in disease. Immunol Today. Oct. 1993;14(10):506-512.
Gertzberg et al., NAD(P)H oxidase mediates the endothelial barrier dysfunction induced by TNF-alpha. Am J Physiol Lung Cell Mol Physiol. Jan. 2004;286(1):L37-48.
Gimbrone, Vascular Endothelium: An Integrator of Pathophysiologic Stimuli in Atherosclerosis. Am J Cardiol. Feb. 23, 1995;75(6):67B-70B.
Glas et al., The diagnostic odds ration: a single indicator of test performance. J Clin Epidemiol. Nov. 2003;56 (11):1129-1135.
Higashi et al., The Receptors for Advanced Glycation End Products Mediates the Chemotaxis of Rabbit Smooth Muscle Cells. Diabetes. Mar. 1997;46(3):463-472.
Hofmann et al., RAGE Mediates a Novel Proinflammatory Axis: A central Cell Surface Receptor for S100/Calgranulin Polypeptides. Cell. Jun. 25, 1999;97(7):889-901.
Huttunen et al., Coregulation of Neurite Outgrowth and Cell Survival by Amphoterin and S100 Proteins through Receptor for Advanced Glycation End Products (RAGE) Activation. J Biol Chem. Dec. 22, 2000;275(51):40096-40105.
Kaneko et al., Probucol Downregulates E-Selectin Expression on Cultured Human Vascular Endothelial Cells. Arterioscler Thromb Vasc Biol. Aug. 1996;16(8):1047-1051.
Kastrati et al., Restenosis After Coronary Placement of Various Stent Types. Am J Cardiol. Jan. 1, 2001;87(1):34-39.
Libby and Hansson, Involvement of the Immune System in Human Atherogenesis: Current Knowledge and Unanswered Questions. Lab Invest. Jan. 1991;64(1):5-15.
Martin et al., Vitamin E Inhibits Low-Density Lipoprotein-Induced Adhesion of Monocytes to Human Aortic Endothelial Cells In Vitro. Arterioscler Thromb Vasc Biol. Mar. 1997;17(3):429-436.
Reznikov et al., Effect of advances glycation and products on endotoxin-induced TNF-alpha, IL-1beta and IL-8 in human peripheral blood mononuclear cells. Clin Nephrol. May 2004;61(5):324-336.
Rosca et al., Glycation of mitochondrial proteins from diabetic rat kidney is associated with excess superoxide formation. Am J Physiol Renal Physiol. Aug. 2005;289(2):F420-F430.
Ross, Rous-Whipple Award Lecture. Atherosclerosis: A Defense Mechanism Gone Awry. Am J Pathol. Oct. 1993;143(4):987-1002.
Sakaguchi et al., Central role of RAGE-dependent neointimal expansion in arterial restenosis. J Clin Invest. Apr. 2003;111(7):959-972.
Steinberg et al., Of Human Atherosclerosis. Summary of the Proceedings of a National Heart, Lung, and Blood Institute Workshop: Sep. 5-6, 1991, Bethesda, Maryland. Circulation. Jun. 1992;85(6):2337-2344.
Thorpe and Baynes, Maillard reaction products in tissue proteins: new products and new perspectives. Amino Acids.Dec. 2003;25(3-4):275-281.
Wang et al., Neutrophils in Innate Immunity. Semin Respir Crit Care Med. Feb. 2004;25(1):33-41.
Wendt et al., Accelerated Atherosclerosis and Vascular Inflammation Develop in APO E Null Mice with Type 2 Diabetes. Abstracts from Scientific Sessions 2000:1125.
Yonekura et al., Novel Splice variants of the receptor for advanced glycation end-products expressed in human vascular endothelial cells and pericytes, and their putative roles in diabetes-induced vascular injury. Mar. 15, 2003;370 (Pt 3):1097-1109.
Yuo et al., (1991) Stimulation and Priming of Human Neutrophils by Interleukin-8: Cooperation With Tumor Necrosis Factor and Colony-Stimulating Factors. Blood. Nov. 15, 1991;78(10):2708-2714.
Zhou et al. (2003) Receptor for AGE (RAGE) Mediates Neointimal Formation in Response to Arterial Injury. Circulation.May 6, 2003;107(17):2238-2243.
Neumann et al., High molecular weight hyaluronic acid inhibits advanced glycation endproduct-induced NF-kappaB activation and cytokine expression. FEBS Lett. Jun. 25, 1999;453(3):283-287.
Nwariaku et al., NADPH oxidase mediates vascular endothelial cadherin phosphorylation and endothelial dysfunction. Blood. Nov. 15, 2004;104(10):3214-3220.
Prasad and Kalra, Oxygen free radicals and hypercholesterolemic atherosclerosis: Effect of vitamin E. Am Heart J. Apr. 1993;125(4):958-973.
Prasad, Reduction of Serum Cholesterol and Hypercholesterolemic Atherosclerosis in Rabbits by Secoisolariciresinol Diglucoside Isolated from Flaxseed. Circulation. Mar. 16, 1999;99(10):1355-1362.
Prasad, Hypocholesterolemic and antiatherosclerotic effect of flax lignan complex isolated from flaxseed. Atherosclerosis. Apr. 2005;179(2):269-275.
Prasad, Soluble receptor for Advanced Glycation End Products (sRAGE) and Cardiovascular Disease. International Journal of Angiology. 2006;15:57-68.
Prasad and Lee, Suppression of hypercholesterolemic atherosclerosis by pentoxifylline and its mechanism. Atherosclerosis. Jun. 2007;192(2)313-322.
Basta et al., Plasma N-epsilon-(carboxymethyl)lysine levels are associated with the extent of vessel injury after coronary arterial stenting. Coron Artery Dis. Aug. 2008;19(5):299-305.
Guidelines for cost effective EPOQUE use: 1 page.
Kozinski et al., Percutaneous coronary intervention triggers a systemic inflammatory response in patients treated for in-stent restenosis: comparison with stable and unstable angina. Inflamm Res. May 2005;54(5):187-193.
Nawroth et al., Atherosclerosis and Restenosis: Is There a Role for RAGE? Curr Diab Rep. Feb. 2005;5(1):11-16.
Extended European Search Report issued in PCT/CA2010000833 dated Jan. 7, 2013.
Choi et al., Serum levels of advanced glycation end products are associated with in-stent restenosis in diabetic patients. Yonsei Med J. Feb. 28, 2005;46(1):78-85.
McNair et al., Low levels of soluble receptor for advanced glycation end products in non-ST elevation myocardial infarction patients. Int J Anglo!. 2009 Winter;18(4):187-192.
Mcnair et al., Soluble Receptors for Advanced Glycation End Products (Srage) as a Predictor of Restenosis Following Percutaneous Coronary Intervention. Clin Cardiol. Nov. 2010;33(11):678-685.
Prasad et al., Soluble Receptors for Advanced Glycation End Products (Srage) and Cardiovascular Disease. Int J Angiol. Jan. 2006;15:57-68.
Wendt et al., Receptor for advanced glycation endproducts (RAGE) and vascular inflammation: Insights into the pathogenesis of macrovascular complications in diabetes. Curr Atheroscler Rep. May 2002;4(3):228-237.

Sensitivity, Specificity, Predictive Values and Accuracy of sRAGE and AGE/sRAGE tests for NSTEMI Patients

|           | Sensitivity | Specificity | PPV  | NPV  | Accuracy |
|-----------|-------------|-------------|------|------|----------|
| sRAGE     | 59%         | 100%        | 100% | 100% | 74%      |
| AGE/sRAGE | 85%         | 91%         | 97%  | 67%  | 86%      |

Figure 12

Sensitivity, Specificity, Predictive Values and Accuracy of sRAGE and
AGE/sRAGE tests for Post-PCI Restenosis in NSTEMI Patients

|  | Sensitivity | Specificity | PPV | NPV | Accuracy |
| --- | --- | --- | --- | --- | --- |
| sRAGE | 100% | 83% | 85% | 100% | 91% |
| AGE/sRAGE | 81% | 94% | 93% | 84% | 88% |

Figure 13

DIAGNOSIS OF RESTENOSIS IN PATIENTS UNDERGOING PERCUTANEOUS CORONARY INTERVENTION

RELATED APPLICATIONS

This application is filed under 35 U.S.C. §371 as the U.S. national phase of International Application No. PCT/CA2010/000833, filed Jun. 2, 2010, which designated the U.S. and claims the benefit of priority to U.S. Provisional Application Ser. No. 61/183,613, filed Jun. 3, 2009, each of which is hereby incorporated in its entirety including all tables, figures, and claims.

FIELD OF THE INVENTION

The field of the invention generally relates to compounds, compositions, methods and/or kits for determining and/or predicting and/or diagnosing restenosis in patients who undergo percutaneous coronary intervention.

BACKGROUND OF THE INVENTION

Advanced Glycation Endproducts (AGEs) act on cell receptors for AGEs (RAGE). There are three forms of RAGE (2, 3): full length, N-truncated and C-truncated soluble receptors for AGEs (sRAGE).

The interaction of full-length RAGE and AGEs results in increased expression of proinflammatory mediators, activation of nuclear factor kappa B (NF-κB) and induction of oxidative stress. The interaction leads to increased expression of adhesion molecules, including soluble vascular cell adhesion molecule-1 (sVCAM-1) and cytokines including tumor necrosis factor-alpha (TNF-α) (2, 4, 5, 6). Interaction of AGEs with RAGE results in activation of NF-κB (4) which in turn leads to increased expression of proinflammatory genes for adhesion molecules and cytokines (2). The interaction also generates oxygen radicals (7).

The function of N-truncated RAGE is poorly understood.

sRAGE lacks a transmembrane domain, and circulates in the plasma (8). sRAGE acts as a decoy for RAGE ligands and this occurs by sequestering circulating RAGE ligands or by competing with full length RAGE for ligand binding (9). It has a protective role by preventing the activation of full length RAGE which could otherwise result in enhanced oxidative stress and activation of NF-κB, cytokines and adhesion molecules, leading to tissue damage and development of atherosclerosis.

Restenosis is a major problem for long-term success after percutaneous coronary interventions (PCI) such as angioplasty and stenting (10). Restenosis following PCI is associated with neointimal hyperplasia. Balloon injury in the carotid artery and arterial endothelial denudation in animal models increase the levels of RAGE and AGEs in the arterial wall and produce neointimal hyperplasia (11, 12). The interaction of RAGE and AGEs results in increased expression of cell adhesion molecules, cytokines, NF-κB, matrix metalloproteinase-9 (MMP-9) and increased levels of tissue factor and oxidative stress (2). These substances are involved in the development of atherosclerosis, clot formation and plaque instability.

Currently, the available techniques for identifying patients with coronary artery disease include: i) electrocardiography, ii) exercise tolerance test, iii) coronary angiography, iv) multi-detector CT angiography, and v) radionucleide imaging. However, these techniques are time-consuming and expensive.

Presently, there is no technology available for predicting restenosis in patients who undergo angioplasty and stent implantation.

It is, therefore, desirable to provide compounds, compositions, methods and/or kits for predicting/diagnosing restenosis in patients who undergo PCI, including stent implantation.

This background information is provided for the purpose of making know information believed by the applicant to be of possible relevance to the present invention. No admission is necessarily intended, nor should it be construed, that any of the preceding information constitutes prior art against the present invention.

SUMMARY OF THE INVENTION

An object of the present invention is to provide compounds, compositions, methods and/or kits for determining and/or predicting and/or diagnosing restenosis in patients who undergo percutaneous coronary intervention.

In accordance with one aspect of the present invention there is provided a method comprising: a) obtaining a serum sample from a subject; b) contacting the sample with an antibody to sRAGE to form a complex between the antibody and sRAGE present in the sample; c) measuring the complexes formed to determine an amount of sRAGE in the sample; and d) determining a development of acute coronary syndrome (ACS) in the subject, wherein the development of ACS is indicated by the level of sRAGE in the sample.

In a specific aspect, instrumentation having a detector set to detect the complex formed between said antibody and said sRAGE in said sample is used to determine an amount of complex in the sample. In another specific aspect, said instrumentation is a spectrophotometer, spectrofluorometer or optical/electrochemical device.

In one aspect, said ACS is NSTEMI, STEMI or acute angina.

In accordance with another aspect of the present invention there is provided a method comprising: a) obtaining a serum sample from a subject with ACS; b) contacting the sample with an antibody to a biomarker within said sample to form a complex between the antibody and said biomarker; c) measuring the complexes formed to determine an amount of said biomarker in the sample; and d) determining the development of post-PCI restenosis, wherein the development of restenosis is indicated by the amount of said biomarker in said sample.

In a specific aspect, instrumentation having a detector set to detect the complex formed between said antibody and the biomarker in said sample is used to determine an amount of complex in the sample. In anther specific aspect, said instrumentation is a spectrophotometer, spectrofluorometer or optical/electrochemical device.

In another specific aspect, said antibody is an antibody to sRAGE, TNF-α, sVCAM-1 or AGE. The measurement of the complexes formed determine the amount of sRAGE, TNF-α, sVCAM-1 or AGE in the sample. In a specific aspect, said subject is a human. In another specific aspect, said ACS is NSTEMI, STEMI or acute angina.

In accordance with another aspect of the present invention there is provided a method comprising: a) obtaining a serum sample from a subject with ACS; b) contacting a first portion of said sample with an antibody to sRAGE to form a complex between the antibody and sRAGE present in the sample; c) contacting a second portion of the sample with an antibody to AGE to form a complex between the antibody and AGE present in the sample; d) measuring the complexes formed to determine an amount of sRAGE in the sample and the amount of AGE in the sample; and e) determining the development of post-PCI restenosis, wherein the development of restenosis is indicated by the ratio of AGE/sRAGE in the sample.

In one aspect instrumentation having a detector set to detect the complex formed between said antibody and the biomarker in said sample is used to determiner an amount of complex in the sample. In another aspect, said instrumentation is a spectrophotometer, spectrofluorometer or optical/electrochemical device.

In another aspect, said subject is a human. In another aspect said ACS is NSTEMI, STEMI or acute angina.

In accordance with another aspect of the present invention there is provided a method comprising, administering to a subject for treatment of restenosis an effective therapeutic amount of sRAGE and/or an agent that (i) increases the amount of sRAGE in the subject and/or (ii) decreases the amount of AGE in the subject, indicated by the presence of a low level of sRAGE or high ratio of AGE/sRAGE in a serum sample of a patient.

In one aspect said agent to increase the amount of sRAGE in the subject is selected from ramipril, atorvastatin or methotrexate.

In one aspect the agent to lower the amount of AGE in the subject is telmisartan, atorvastatin, amino-guanidine, pyridoxamine or pimagedine.

In accordance with another aspect of the present invention there is provided a kit, comprising: a) instructions for determining the amount of sRAGE and AGE present in serum of an ACS patient; b) reagents for measuring the serum values of the concentration of sRAGE and AGE; and wherein the restenosis is indicated by a ratio of AGE/sRAGE in the sample.

In one aspect said reagents are antibodies to sRAGE and AGE.

In one aspect the ratio of AGE/sRAGE is determined by a) contacting a first portion of said sample with an antibody to sRAGE to form a complex between the antibody and sRAGE present in the sample; b) contacting a second portion of the sample with an antibody to AGE to form a complex between the antibody and AGE present in the sample; c) measuring the complexes formed to determine an amount of sRAGE in the sample and the amount of AGE in the sample; and d) determining the development of post-PCI restenosis, wherein the development of restenosis is indicated by the ratio of AGE/sRAGE in the sample.

In one aspect, wherein instrumentation having a detector set to detect the complex formed between said antibody and the biomarker in said sample is used to determiner an amount of complex in the sample. In another aspect said instrumentation is a spectrophotometer, spectrofluorometer or optical/electrochemical device. In another aspect said ACS is NSTEMI, STEMI or acute angina.

In accordance with one aspect of the present invention, there is provided a method comprising: a) obtaining a serum sample from a subject; b) contacting the sample with an antibody to sRAGE to form a complex between the antibody and sRAGE present in the sample; c) measuring the complexes formed to determine an amount of sRAGE in the sample; and d) determining a development of ACS in the subject, wherein the development of ACS is indicated by the level of sRAGE in the sample.

In accordance with one aspect of the present invention, there is provided a method comprising: a) obtaining a serum sample from a subject with acute coronary syndrome (ACS) undergoing PCI; b) contacting the sample with an antibody to sRAGE to form a complex between the antibody and sRAGE present in the sample; c) measuring the complexes formed to determine an amount of sRAGE in the sample; and d) determining a development of post-PCI restenosis in the subject, wherein the development of restenosis is indicated by the level of sRAGE in the sample.

In accordance with another aspect of the present invention, there is provided a method comprising: a) obtaining a serum sample from a subject with ACS; b) analyzing the sample and a control using a machine wherein said machine is a spectrophotometer, spectrofluorometer and/or optical/electrochemical device having a detector set to detect a complex formed between an antibody to sRAGE and the sample to obtain an amount of total sRAGE in the sample; and c) determining a development of post-PCI restenosis in the subject, wherein the development of restenosis is indicated by the level of sRAGE in the sample.

In another aspect of the present invention there is provided a method comprising: a) obtaining a serum sample from a subject with ACS; b) contacting a first portion of the sample with an antibody to sRAGE to form a complex between the antibody and sRAGE present in the sample; c) contacting a second portion of the sample with an antibody to AGE to form a complex between the antibody and AGE present in the sample; d) measuring the complexes formed to determine an amount of sRAGE in the sample and the amount of AGE in the sample; and d) determining a development of post-PCI restenosis in the subject, wherein the development of restenosis is indicated by the level of the ratio of AGE/sRAGE in the sample.

In accordance with another aspect of the present invention there is provided a method comprising: a) obtaining a serum sample from a subject with ACS; b) analyzing the sample and a control using a spectrophotometer, spectrofluorometer and/or optical/electrochemical device having a detector set to detect (i) a complex formed between an antibody to sRAGE and the sample to obtain an amount of total sRAGE in the sample and (ii) a complex formed between an antibody to AGE and the sample to obtain an amount of total AGE in the sample; and c) determining a development of post-PCI restenosis in the subject, wherein the development of restenosis is indicated by the level of the ratio of AGE/sRAGE in the sample.

In one aspect of the present invention, the ACS is non-ST-elevated myocardial infarction (NSTEMI), ST-elevated myocardial infarction (STEMI) or unstable angina. In yet another aspect, the ACS is NSTEMI.

In an accordance with a specific aspect of the present invention, said machine is a Biotek (EL808) Plate reader.

In another aspect of the present invention there is provided a method comprising: a) obtaining a serum sample from a subject with ACS; and b) analyzing the sample to identify a level of sRAGE and AGE, wherein a development of post-PCI restenosis in the subject is indicated by the ratio of AGE/sRAGE in the sample.

In another aspect of the present invention there is provided a method comprising: a) obtaining a serum sample from a subject with ACS; and b) analyzing the sample to identify a level of sRAGE, wherein a development of post-PCI restenosis in the subject is indicated by the level of sRAGE in the sample.

In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method comprising, administering to a subject for treatment of restenosis an effective therapeutic amount of sRAGE and/or an agent that (i) increases the amount of sRAGE in the subject and/or (ii) decreases the amount of AGE in the subject, indicated by the presence of a low level of sRAGE in a serum sample of a patient.

In another aspect of the present invention there is provided a method comprising, administering to a subject for treatment of restenosis an effective therapeutic amount of sRAGE and/or an agent that (i) increases the amount of sRAGE in the subject and/or (ii) decreases the amount of AGE in the subject, indicated by the high ratio of the amount of AGE/sRAGE in a serum sample of a patient.

In another aspect of the present invention there is provided a method comprising: a) obtaining a serum sample from a subject with ACS; and b) contacting the sample with an antibody to sRAGE to identify a complex formed by the antibody and sRAGE present in the sample, wherein the level of sRAGE indicates whether alternate and/or additional treatment is required. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method comprising: a) obtaining a serum sample from a subject with ACS; b) contacting a first portion of the sample with an antibody to sRAGE to identify a complex formed by the antibody and sRAGE present in the sample, and c) contacting a second portion of the sample with an antibody to AGE to identify a complex formed by the antibody and AGE present in the sample, wherein the ratio of AGE/sRAGE indicates whether the subject requires alternate and/or additional treatment. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method comprising: administering sRAGE and/or an agent that (i) increases the amount of sRAGE in the subject and/or (ii) decreases the amount of AGE in the subject to a subject suffering from ACS, wherein the subject's serum is known to contain a low level of sRAGE. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method comprising: administering sRAGE and/or an agent that (i) increases the amount of sRAGE in the subject and/or (ii) decreases the amount of AGE in the subject to a subject suffering from ACS, where the subject's serum is known to contain a high level of AGE/sRAGE. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method of determining efficacy of treatment with PCI comprising: identifying a complex formed by an antibody and sRAGE present in a sample from a subject having ACS, wherein a high level of sRAGE indicates effective treatment. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method of determining efficacy of treatment with PCI comprising: identifying a complex formed by (i) an antibody and sRAGE present in a sample and (ii) an antibody and AGE present in a sample, from a subject having ACS, wherein a low ratio of AGE/sRAGE indicates effective treatment. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method for identifying a human subject having ACS, the method comprising: detecting a level of expression of sRAGE in a test sample, wherein the test sample is derived from serum; and comparing the level of expression of the sRAGE in the test sample with a level of expression of sRAGE a control non-ACS sample; wherein an high level of expression of sRAGE in the test sample relative to the level of expression of the sRAGE in the control is indicative of ACS in that subject. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a method for assessing the prognosis of a human subject having ACS, the method comprising: detecting (i) a level of expression of sRAGE in a test sample and (ii) a level of AGE in the test sample, wherein the test sample is derived from serum; and comparing the ratio of expression of the AGE/sRAGE in the test sample with a level of expression of AGE/sRAGE a control non-ACS sample; wherein an high level of AGE/sRAGE in the test sample relative to the level of expression of the sRAGE in the control is indicative of a poor prognosis for the subject. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a kit for diagnosis of post-PCI restenosis, comprising: a) instructions for determining the amount of sRAGE present in serum of an ACS patient; b) reagents for measuring the serum values of the concentration of sRAGE; and wherein the diagnosis is indicated by the level of sRAGE in the sample. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a kit for diagnosis of post-PCI restenosis, comprising: a) instructions for determining the amount of sRAGE and AGE present in serum of an ACS patient; b) reagents for measuring the serum values of the concentration of sRAGE and AGE; and wherein the diagnosis is indicated by the level of AGE/sRAGE in the sample. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a use of an antibody to sRAGE to detect the amount of sRAGE-antibody complex in a serum sample from a patient with ACS, wherein the level of sRAGE indicates whether the subject requires alternate and/or additional treatment. In one aspect of the present invention, the ACS is non-ST-elevated myocardial infarction (NSTEMI), ST-elevated myocardial infarction (STEMI) or unstable angina. In yet another aspect, the ACS is NSTEMI.

In another aspect of the present invention there is provided a use of an antibody to sRAGE and AGE to detect the amount of sRAGE-antibody complex and AGE-antibody complex in a serum sample from a patient with ACS, wherein the ratio of AGE/sRAGE indicates whether the subject requires alternate and/or additional treatment. In one aspect of the present invention, the ACS is non-ST-elevated myocardial infarction (NSTEMI), ST-elevated myocardial infarction (STEMI) or unstable angina. In yet another aspect, the ACS is NSTEMI.

BRIEF DESCRIPTION OF THE DRAWINGS

Embodiments of the present invention will now be described, by way of example only, with reference to the attached Figures, wherein:

FIG. 12 is a table depicting sensitivity, specifity, predictive values and accuracy of sRAGE and AGE/sRAGE tests for NSTEMI Patients; and FIG. 13 is a table depicting sensitivity, specificity, predictive values and accuracy of sRAGE and AGE/sRAGE tests for Post-PCI Restenosis in NSTEMI Patients.

DETAILED DESCRIPTION

Figure 1:
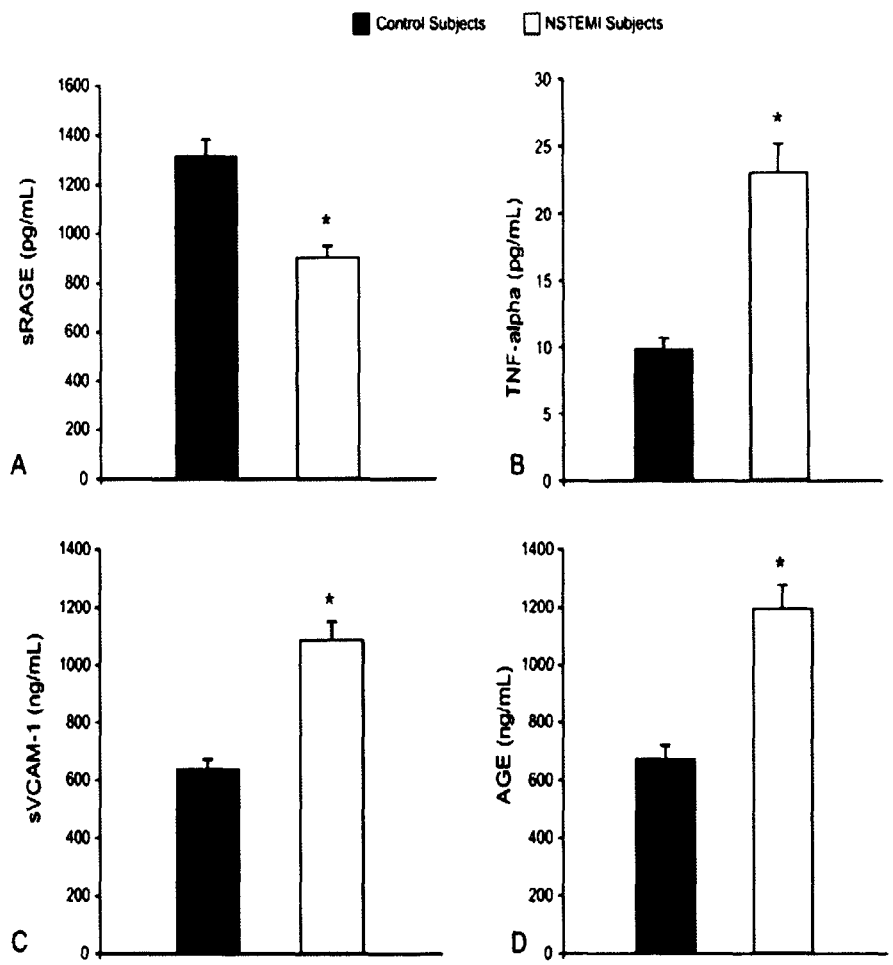
FIG. 1 depicts serum levels of soluble receptor for advanced glycation end products (sRAGE) (Panel A), tumor necrosis factor-alpha (TNF-α) (Panel B), soluble vascular cell adhesion molecule-1 (sVCAM-1) (Panel C) and advanced glycation end products (AGE) (Panel D) in control and non-ST-elevation myocardial infarction (NSTEMI) subjects. The results are expressed as mean±SE. *p<0.05, control vs. NSTEMI.

As will be described in more detail below, the present invention relates to compounds, compositions, methods and kits for the diagnosis and/or prognosis and/or or therapeutic monitoring of acute coronary syndrome (ACS), peripheral vascular diseases and cerebral vascular diseases in human patients.

In one embodiment, the ACS is non-ST-elevated myocardial infarction (NSTEMI), ST-elevated myocardial infarction (STEMI) or unstable angina. In a specific example, the ACS is NSTEMI.

In one example, a serum sample is obtained from a subject afflicted with ACS. In a specific example, a serum sample is obtained from a subject afflicted with NSTEMI. Methods for serum collection are well known to the skilled worker.

The term "subject" as used herein, refers to any human or animal who would benefit from treatment and/or diagnosis. Non-limiting examples of a subject include humans, non-human mammals, companion animals, livestock and the like.

Biochemical markers (or biomarkes) are used to assay and/or assess the serum collected from the subject(s). In one example, antibodies are used to detect the biochemical markers within the serum collected from the subject(s).

Antibodies of the present invention are immunoreactive or immunospecific for and therefore specifically and selectively bind to a protein of interest, and include, for example, human sRAGE, TNF-α, sVCAM-1 and/or AGE protein. Antibodies which are immunoreactive and immunospecific for human human sRAGE, TNF-α, sVCAM-1 and/or AGE protein are preferred. Antibodies for human sRAGE, TNF-α, sVCAM-1 and/or AGE protein are preferably immunospecific—i.e., not substantially cross-reactive with related materials. The term "antibody" encompasses all types of antibodies (e.g., monoclonal and polyclonal).

The term "binds specifically" as used herein is meant high avidity and/or high affinity binding of an antibody to a specific polypeptide, e.g., epitope of sRAGE, TNF-α, sVCAM-1 and/or AGE protein. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level. Such weak binding, or background binding, is readily discernible from the specific antibody binding to the compound or polypeptide of interest, e.g., by use of appropriate controls, as would be familiar to the worker skilled in the art.

In a specific example, the detection and/or measurement of the biochemical marker(s) within the collected serum is carried out using an enzyme-linked immunosorbent assay (ELISA assay). It will be clear to the skilled worker that other immuno assays, both qualitative or quantitative assays, can be used in the present invention.

In one example of the present invention, sRAGE and TNF-α is measured using commercially available enzyme-linked immunoabsorbent assay (ELISA) kits (R&D Systems, Inc., Minneapolis, Minn.), sVCAM-1 is measured using ELISA kits (Abeam, Inc., Cambridge, Mass., USA). AGE levels are measured using human AGE ELISA kits (BIOPCR, Beijing Zhonghao Shidai Co., Ltd., Beijing, China).

In another example, sRAGE is measured using commercially available ELISA kits from BioVendor Research and Diagnostic Products (Candler, N.C., USA). In another example, TNF-α is measured using commercially ELISA kits from Abnova (Walnut, Calif. 91789 USA), BD Biosciences, Cayman Chemicals (Cayman Chemical Company, 1180 East Ellsworth road, Ann Arbor, Mich. 48108), Antigenix America (Huntington Station, N.Y. 11746) or BioVendor Research and Diagnostic Products (Candler, N.C., USA).

In another example, sVCAM-1 is measured using commercially available ELISA kits from Cell Sciences, Diaclone or Invitrogen.

A variety of machines and/or instrumentation are used to detect and/or measure the biochemical marker in the serum sample. Suitable machines and/or instrumentation includes a spectrophotometer, spectrofluorometer and/or optical/electrochemical device.

In accordance with a specific example of the present invention, the detection of sRAGE, AGE, sVCAM-1 and/or TNF-α carried out with a Biotek (EL808) Plate reader. In another example an EIA analyzer is used.

The detection of the sRAGE, AGE, sVCAM-1 and/or TNF-α in the serum sample would be well known to the skilled worker. In one example, the ELISA kits are used according to the manufactures instructions.

In one example, there is provided a method comprising: a) obtaining a serum sample from a subject with ACS; b) contacting the sample with an antibody to sRAGE to form a complex between the antibody and sRAGE present in the sample; c) measuring the complexes formed to determine an amount of sRAGE in the sample; and d) determining the development of post-PCI restenosis, wherein the development of restenosis is indicated by the level of sRAGE in the sample. In a specific example, the subject is a human with NSTEMI, STEMI or acute angina. In a specific embodiment, the serum sample is from a subject with NSTEMI and measurement of the complexes formed determine the amount of sRAGE in the sample.

In another example, there is provided a method comprising: a) obtaining a serum sample from a subject with ACS; b) contacting the sample with an antibody to TNF-α to form a complex between the antibody and TNF-α present in the sample; c) measuring the complexes formed to determine an amount of TNF-α in the sample; and d) determining the development of post-PCI restenosis, wherein the development of restenosis is indicated by the level of TNF-α in the sample. In a specific example, the subject is a human with NSTEMI, STEMI or acute angina. In a specific embodiment, the serum sample is from a subject with NSTEMI and measurement of the complexes formed determine the amount of TNF-α in the sample.

In another example, there is provided a method comprising: a) obtaining a serum sample from a subject with ACS; b) contacting the sample with an antibody to sVCAM-1 to form a complex between the antibody and sVCAM-1 present in the sample; c) measuring the complexes formed to determine an amount of sVCAM-1 in the sample; and d) determining the development of post-PCI restenosis, wherein the development of restenosis is indicated by the level of sVCAM-1 in the sample. In a specific example, the subject is a human with NSTEMI, STEMI or acute angina. In a specific embodiment, the serum sample is from a subject with NSTEMI and measurement of the complexes formed determine the amount of sVCAM-1 in the sample.

In another example, there is provided a method comprising: a) obtaining a serum sample from a subject with ACS; b) contacting the sample with an antibody to AGE to form a complex between the antibody and AGE present in the sample; c) measuring the complexes formed to determine an amount of AGE in the sample; and d) determining the development of post-PCI restenosis, wherein the development of restenosis is indicated by the level of AGE in the sample. In a specific example, the subject is a human with NSTEMI, STEMI or acute angina. In a specific embodiment, the serum sample is from a subject with NSTEMI and measurement of the complexes formed determine the amount of AGE in the sample.

In yet another example, there is provided a method comprising: a) obtaining a serum sample from a subject with ACS; b) contacting a first portion of the sample with an antibody to sRAGE to form a complex between the antibody and sRAGE present in the sample; c) contacting a second portion of the sample with an antibody to AGE to form a complex between the antibogy and AGE present in the sample; d) measuring the complexes formed to determine an amount of sRAGE in the sample and the amount of AGE in the sample; and e) determining the development of post-PCI restenosis, wherein the development of restenosis is indicated by the level of AGE/sRAGE in the sample. In a specific example, the subject is a human with NSTEMI, STEMI or acute angina. In a specific embodiment, the serum sample is from a subject with NSTEMI and measurement of the complexes formed determine the amount of sRAGE and AGE in the sample.

The test sample, and a control sample if present, are analyzed using a spectrophotometer, spectrofluorometer or optical/electrochemical device having a detector set to detect a complex formed between an antibody (e.g., sRAGE, AGE, TNF-α, sVCAM-1) and the sample to obtain an amount of complex in the sample. In a specific example, a Biotek (EL808) Plate reader is used.

Control Subjects vs. Patients with ASC (NSTEMI)

In one example, the levels of serum sRAGE in patients with ACS were significantly lower than those in control subjects.

In another example, the levels of serum TNF-α in ACS patient are significantly higher than those in control patients.

In another example, the levels of serum sVCAM-1 in patient with ACS are significantly higher than those in control subjects.

In another example, the levels of serum AGE in ACS patients are significantly higher than those in control subjects.

In another example, levels of serum sRAGE are negatively correlated with the number of diseased vessels, while the levels of serum AGE, AGE/sRAGE, TNF-α and sVCAM-1 are positively correlated with the number of diseased vessels.

In another example, the ratio of serum AGE/sRAGE in patients are significantly higher than those in control subjects.

In another example, there is an inverse relationships between serum sRAGE and AGE, serum sRAGE and AGE/sRAGE, serum sRAGE and TNF-α, and serum sRAGE and sVCAM-1, in both control subjects and patients with NSTEMI.

In yet another experiment, the sensitivity, specificity, negative predictive value, positive predictive value and accuracy of the sRAGE test in identifying patients with ACS (NSTEMI) were 59%, 100%, 100%, 100% and 74%, respectively. The sensitivity, specificity, negative predictive value, positive predictive value and accuracy of the AGE/sRAGE test were 85%, 91%, 67%, 97% and 86%, respectively, in identifying patients with ACS (NSTEMI).

NSTEMI Patient with or without Post-PCI Restenosis

In one example, NSTEMI patients with restenosis had lower pre-PCI levels of sRAGE and higher levels of AGE, AGE/sRAGE, TNF-α and sVCAM-1 compared to patients without restenosis.

In another example, in NSTEMI patients, the post-PCI levels of serum sRAGE are lower, and of sVCAM-1 and TNF-α are higher in patients with restenosis compared to patients without restenosis. In a specific example, the post-PCI levels of sRAGE are lower, TNF-α higher, and sVCAM-1 unaltered compared to pre-PCI levels in patients who developed restenosis. Pre- and post-PCI levels of sRAGE, TNF-α and sVACM-1 were similar in patients without restenosis.

In another example, serum levels of sRAGE are negatively correlated with serum levels of TNF-α and sVCAM-1, irrespective of pre- and post-PCI status or patients with or without restenosis.

In a specific example, in the case of post-PCI detection, the sensitivity and negative predictive values of pre-PCI sRAGE test in identifying patients with post-PCI restenosis were 100%, while the specificity, positive predictive values and accuracy were 83%, 85% and 91%, respectively. The sensitivity, specificity, positive predictive value, negative predictive value and accuracy of the pre-PCI AGE/sRAGE test were 81%, 94%, 93%, 84% and 88%, respectively.

Treatment options for patients who develop post-PCI restenosis are known to the skilled worker. It will be clear to the skilled worker that those treatment options for patients who are determined to develop post-PCI restenosis using methods of the present application are also suitable for use.

In one example, a subject who is determined to develop post-PCI restenosis is treated with an agent to increase the levels of serum sRAGE in the subject. In one embodiment, the subject is treated with sRAGE and/or treated with an agent(s) to increase the level of serum sRAGE.

Agents to treat post-PCI restenosis to increase serum sRAGE include, but are not limited to, ramipril (an ACE inhibitor), atorvastatin (a lipid lowering agent) or methotrexate.

In one example, a subject who is determined to develop post-PCI restenosis is treated with an agent to decrease the levels of AGEs.

Additional agents to treat post-PCI restenosis include, but are not limited to, telmisartan, atorvastatin, amino-guanidine, pyridoxamine and/or pimagedine, which lower serum AGE.

Alternatively, or in addition to, treatment of a subject comprises the reduction of intake of food(s) that generate and/or promote the development of AGEs (e.g., sugars). Such foods are known to the skilled worker.

Alternatively, or in addition to, treatment of a subject comprises administration of "AGE-breakers", to decrease the amount of AGE-induced cross-linking, which would be known to the skilled worker.

In one example, agents to increase serum sRAGE and agents to decrease levels of AGEs and the reduction of the intake of food(s) that generate and/or promote the development of AGEs are used.

In another aspect of the present invention there is provided a method comprising, administering to a subject for treatment and/or prevention of restenosis an effective therapeutic amount of sRAGE and/or sRAGE inducing agent and/or AGE reducing agent and/or AGE-breaker indicated by the presence of a low level of sRAGE in a serum sample of a patient.

In another aspect of the present invention there is provided a method comprising, administering to a subject for treatment and/or prevention of restenosis an effective therapeutic amount of sRAGE and/or sRAGE inducing agent and/or AGE reducing agent and/or AGE-breaker indicated by the ratio of the amount of AGE/sRAGE in a serum sample of a patient.

The terms "treating" or "lessening the severity" as used herein, may, in one embodiment comprise enhancement of survival, or in another embodiment, halting disease progression, or in another embodiment, delay in disease progression, or in another embodiment, diminishment of pain, or in another embodiment, delay in disease spread to alternate sites, organs or systems, or any clinical benefit.

The method(s) of the present invention can be automated, the data being sent to a computer that analyzes amount of antibody complex in a sample, and the prognosis of patients undergoing PCI being identified.

Methods of the present invention are conveniently practiced by providing the compound(s) and/or composition(s) used in such method in the form of a kit. Such a kit preferably contains the instructions of the use thereof.

To gain a better understanding of the invention described herein, the following examples are set forth. It should be understood that these example are for illustrative purposes only. Therefore, they should not limit the scope of this invention in any way.

EXAMPLE

Methods

A total of 46 consecutive male patients undergoing bare metal stent implantation and 28 age-matched healthy male subjects (63.8±11 years vs. 58.5±22 years SD) were recruited.

Inclusion criteria for patients were as follows:
  i) ACS patients with non-ST-segment elevated myocardial infarction (NSTEMI);
  ii) discrete de novo localized lesions in single or multiple vessels (up to 3 vessels);
  iii) reference coronary artery diameter>2.5 mm;
  iv) bare metal stent implantation;
  v) non-diabetic.

Exclusion criteria were as follows:
  i) acute myocardial infarction within five days;
  ii) aorta-coronary bypass surgery;
  iii) >3 stent implantations;
  iv) inflammatory disease;
  v) valvular heart disease;
  vi) Alzheimer disease;
  vii) current smokers;
  viii) renal dysfunction.

The bare metal stents were implanted in patients undergoing percutaneous coronary intervention (PCI). The patients were put on combined antiplatelet therapy with aspirin (100 mg/day) and clopidogrel (75 mg/day), and lipid-lowering agents (statins). All patients were advised to return for a repeat coronary angiography six months after index coronary intervention. Blood samples were collected for the measurement of sRAGE, AGE, TNF-α and sVCAM-1 before PCI and 6 months post-PCI. Informed consent was obtained from all patients. The project approval was obtained from the University of Saskatchewan Ethics Committee and Saskatoon Health Region (Royal University Hospital).

Measurement of sRAGE, TNF-α, sVCAM-1 and AGE

To obtain serum, seventeen mL of blood was collected from each patient and transferred into 8.5 mL Vacutainer serum separator tubes. Blood samples were allowed to clot and then immediately centrifuged at 1000 rpm for 15 minutes for serum separation. Serum was transferred into labeled tubes and stored at −80° C. until assayed.

The serum levels of sRAGE and TNF-α were measured using commercially available enzyme-linked immunoabsorbent assay (ELISA) kits (R&D Systems, Inc., Minneapolis, Minn.) according to the manufacturer's protocol. sVCAM-1 was measured using ELISA kits (Abcam, Inc., Cambridge, Mass., USA). AGE levels were measured using human AGE ELISA kits (BIOPCR, Beijing Zhonghao Shidai Co., Ltd., Beijing, China).

The results of the ELISA analysis were obtained using a Biotek (EL808) Plate reader.

Angiographic Analysis

Angiography was performed and the angiograms analyzed by two cardiologists blinded to the clinical characteristics of the patients. Reference diameter, minimal lumen diameter, percentage of stenosis, and lesion length were measured using a semi-automated edge counter detection computer analysis system (QCACMS Version 4, Medis Medical Imaging Systems Inc., Lein, The Netherlands). Coronary angiography showed that 16 patients had one vessel disease (1VD), 15 patients had two vessel disease (2VD), and 15 patients had three or more vessel disease (3VD).

Statistical Analysis

Sample size was calculated using two-sided Satterthwaite t-test to have 95% power and 5% alpha level. The data are presented as mean±SE. The data between two groups were compared using the 2-tailed unpaired Student t-test. Single linear univariate correlations (Spearman's Correlation Coefficients) were performed to evaluate the relationships between circulating sRAGE levels and TNF-α, between sRAGE and sVCAM-1, between sRAGE and AGE, and between sRAGE and AGE/sRAGE. The serum levels of sRAGE, AGE, AGE/sRAGE, TNF-α and sVCAM-1 in 1VD, 2VD and 3VD were compared with control. A p value of <0.05 was considered significant. Sensitivity, specificity, positive predictive value, negative predictive value and accuracy of the sRAGE and AGE/sRAGE tests were calculated as described by Glas et al, (14).

Results

A. Control Subjects vs. Patients with ACS (NSTEMI)

1. Serum Levels of sRAGE, TNF-α, sVCAM-1, AGE and AGE/sRAGE

Figure 2:
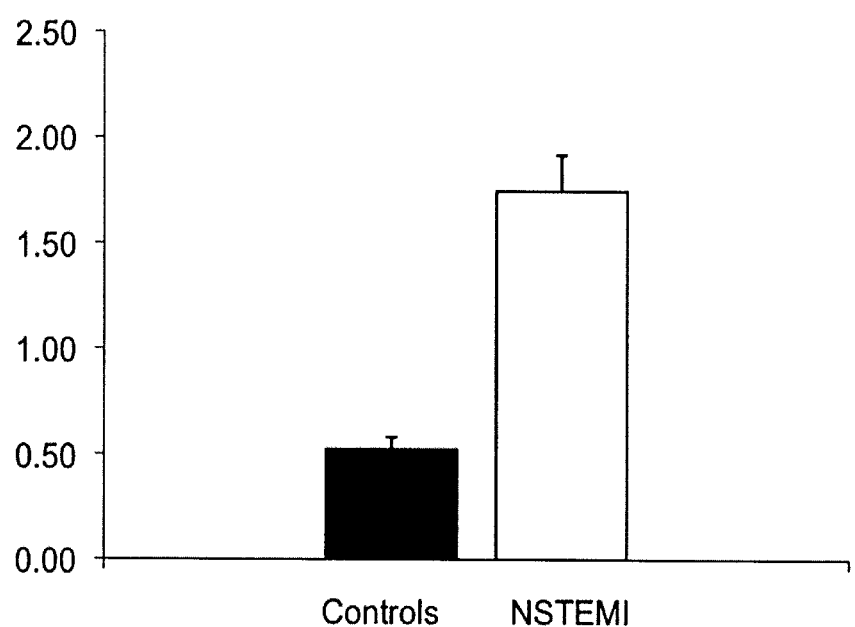
FIG. 2 depicts the ratio of AGE/sRAGE in control and non-ST-levation myocardial infarction (NSTEMI) subjects. The results are expressed as mean±SE. *p<0.05, control vs. NSTEMI

The levels of serum sRAGE, TNF-α, sVCAM-1, AGE and AGE/sRAGE in control subjects and ACS (NSTEMI) patients are summarized in FIGS. 1 and 2. The serum levels of sRAGE in control subjects ranged from 1009 to 1635 pg/ml with a mean±SE of 1287.0±41.5 pg/ml. The serum levels of sRAGE in ACS (NSTEMI) patients ranged from 480 to 1538 pg/ml with a mean±SE of 892.65±50.62 pg/ml. The levels of serum sRAGE in patients with ACS were significantly (p<0.001) lower than those in control subjects.

The serum levels of TNF-α in control subjects ranged between 1.8 and 15.83 pg/ml with a mean±SE of 10.3±0.8 pg/ml, while those in patients with ACS ranged between 6.8 and 58.0 with a mean±SE of 23.1±2.3 pg/ml. The levels of serum TNF-α in ACS patients were significantly (p<0.002) higher than those in control subjects.

The serum levels of sVCAM-1 in control subjects ranged between 212 and 989 ng/ml with a mean±SE of 651.0±35.5 ng/ml, while those in patients with ACS ranged between 261 and 1963, with a mean±SE of 1059.6±70.8 ng/ml. The levels of sVCAM-1 in patients with ACS were significantly (p<0.0003) higher than those in control subjects.

The serum levels of AGE in ACS patients were higher compared to control subjects (1192.5±82.6 vs. 669.4±47.9 ng/ml). The ratio of AGE/sRAGE was 1.72±0.14 in ACS patients and 0.54±0.06 in control subjects, and these values were significantly different from each other.

These data indicate that the serum levels of sRAGE are lower, and those of TNF-α, sVCAM-1, AGE and AGE/sRAGE are higher in ACS patients compared to control subjects.

Figure 3:
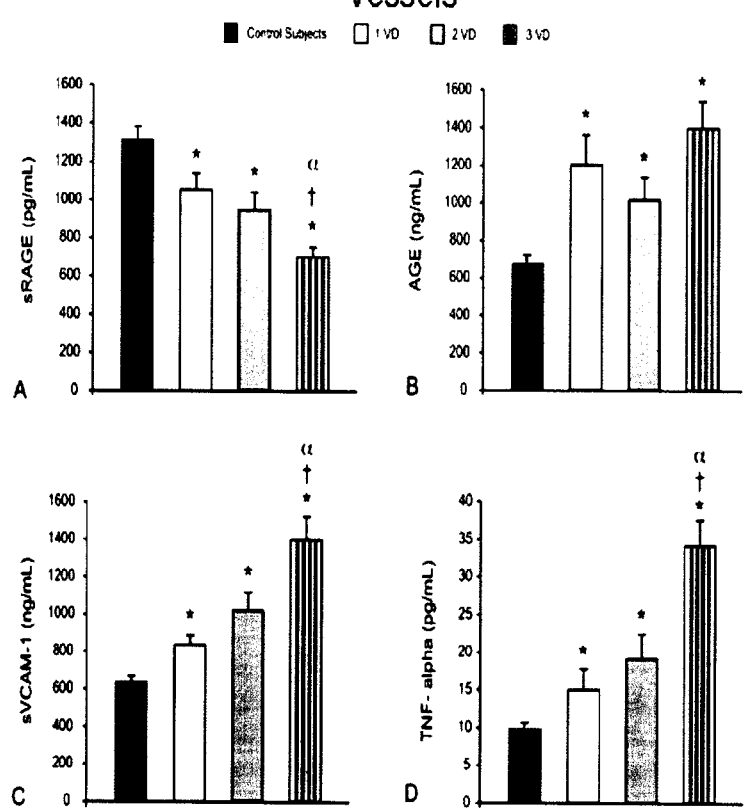
FIG. 3 depicts serum levels of sRAGE (Panel A), TNF-α (Panel D), sVACM-1 (Panel C) and AGE (Panel B) in control subjects and NSTEMI patients with 1VD, 2VD and 3 or more VD. The results are expressed as mean±SE. The notations for sRAGE, TNF-α, sVCAM-1 and AGE are similar to FIG. 1. 1VD, one vessel disease, 2VD, two vessel disease, 3VD, three vessel disease. *p<0.05, control vs. 1VD, 2VD or 3VD. †p<0.05, 1VD vs. 2VD or 3VD. αp<0.05, 2VD vs. 3VD.
Figure 4:
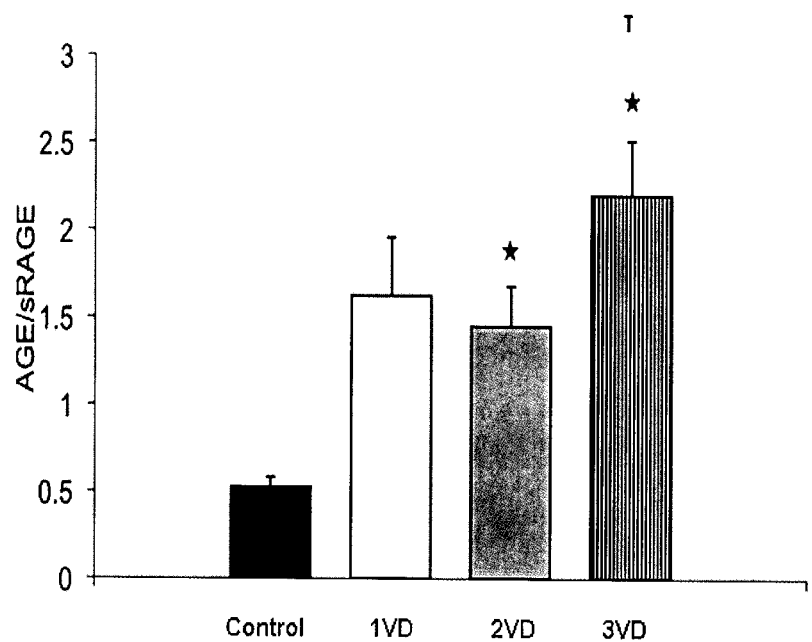
FIG. 4 depicts the ratio of AGE/sRAGE in control subjects and NSTEMI patients with 1VD, 2VD and 3 or more VD. The results are expressed as mean±SE. AGE, advanced glycation end product; sRAGE, soluble receptor for AGE; 1 VD, one vessel disease; 2VD, two vessel disease; 3VD, three vessel disease. *p<0.05, control vs. 1VD, 2VD or 3VD; †p<0.05, 1VD vs. 2VD or 3VD.

2. Relation of sRAGE, AGE, AGE/sRAGE, TNF-α and sVCAM-1 with the Number of Diseased Vessels The levels of sRAGE, TNF-α and sVCAM-1 in relation to the number of diseased vessels are summarized in FIG. 3, while those of AGE and AGE/sRAGE in relation to the number of diseased vessels are summarized in FIG. 4. There was a progressive decrease in the levels of serum sRAGE and progressive increases in the levels of serum AGE, AGE/sRAGE, TNF-α and sVCAM-1, with increases in the number of diseased vessels. These data indicate that levels of serum sRAGE are negatively correlated with the number of diseased vessels, while the levels of serum AGE, AGE/sRAGE, TNF-α and sVCAM-1 are positively correlated with the number of diseased vessels.

3. Correlation of sRAGE to AGE, AGE/sRAGE, TNF-α and sVCAM-1

Figure 5:
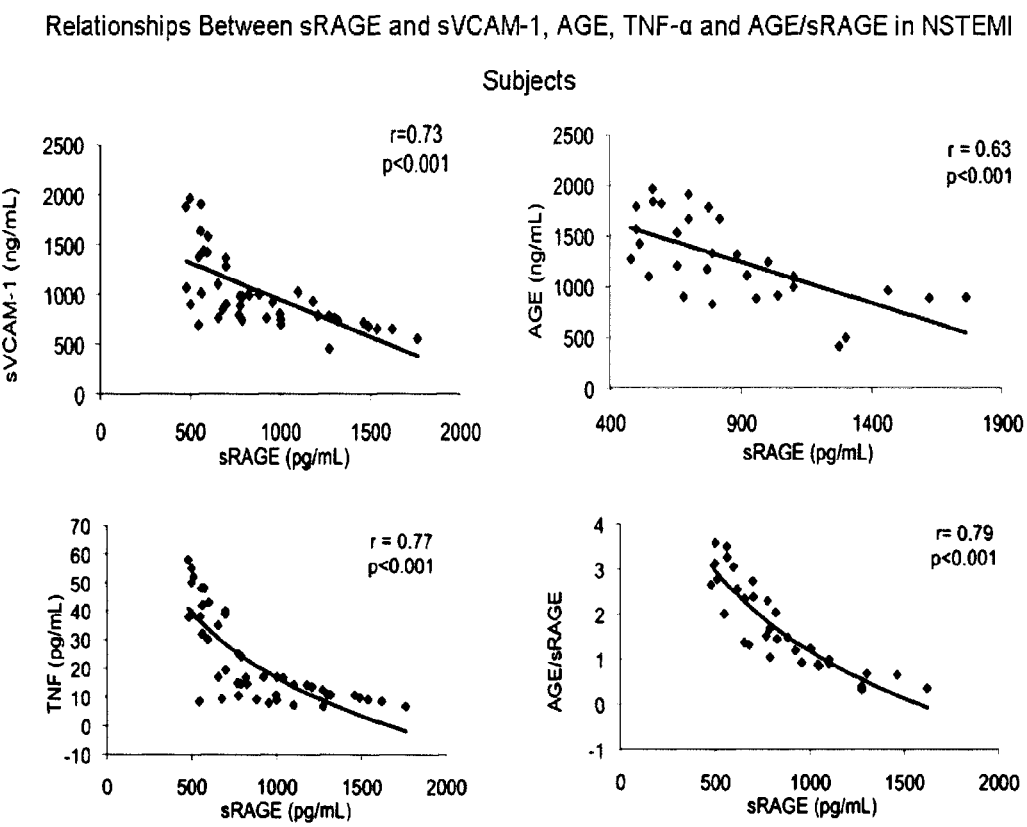
FIG. 5 depicts the relationship between sRAGE and sVCAM-1, AGE, TNF-α and AGE/sRAGE in NSTEMI Subjects.

Correlations between serum sRAGE and AGE, serum sRAGE and AGE/sRAGE, serum sRAGE and TNF-α, and serum sRAGE and sVCAM-1 for patients with ACS are shown in FIG. 5. There are inverse relationships between serum sRAGE and AGE, serum sRAGE and AGE/sRAGE, serum sRAGE and TNF-α, and serum sRAGE and sVCAM-1, with p values of <0.001. Similar inverse relationships between sRAGE and TNF-α and between sRAGE and sVCAM-1 were observed in control subjects (data not shown).

The results show that there are inverse relationships between sRAGE and AGE, sRAGE and AGE/sRAGE, sRAGE and TNF-α, and sRAGE and sVCAM-1 in both control subjects and patients with NSTEMI.

4. Sensitivity, Specificity, Predictive Values and Accuracy of the sRAGE and AGE/sRAGE Test for ACS Patients The data for sensitivity, specificity, negative predictive value, positive predictive value and accuracy of the sRAGE and AGE/sRAGE tests for diagnosis of patients with NSTEMI are given in FIG. 12. Sensitivity refers to probability that a test will be positive in patients with disease. Specificity refers to probability that a test will be negative in individuals without disease. Positive predictive value (PPV) refers to probability that a patient will have disease given a positive test result. Negative Predictive Value (NPV) refers to probability that an individual will not have a disease given a negative rest result. Accuracy refers to probability of correctly identifying subjects. NSTEMI refers to Non-St-elevation myocardial infarction. The sensitivity, specificity, negative predictive value, positive predictive value and accuracy of the sRAGE test in identifying patients with ACS (NSTEMI) were 59%, 100%, 100%, 100% and 74%, respectively. The sensitivity, specificity, negative predictive value, positive predictive value and accuracy of the AGE/sRAGE test were 85%, 91%, 67%, 97% and 86%, respectively, in identifying patients with ACS (NSTEMI).

These data indicate that both sRAGE and AGE/sRAGE tests serve as biomarkers/predictors for identifying patients with ACS (NSTEMI). The sensitivity of AGE/sRAGE is greater than that of sRAGE while the negative predictive value of sRAGE is greater than that of AGE/sRAGE in identifying patients with ACS (NSTEMI).

B. NSTEMI Patients with or without Post-PCI Restenosis

Pre-PCI and post-PCI levels of sRAGE, AGE, AGE/sRAGE, TNF-α and sVCAM-1 were measured in 22 ACS (NSTEMI) patients who developed post-PCI restenosis and 24 NSTEMI patients who did not develop post-PCI restenosis.

In the present study, 50% or more narrowing of implanted stent is considered restenosis. A patient with less than 50% narrowing of a stent is considered a patient without restenosis. Narrowing of lunen diameter measurement is considered restenosis.

1. Pre-PCI Serum Levels of sRAGE, TNF-α, sVCAM-1, AGE and AGE/sRAGE

Figure 6:
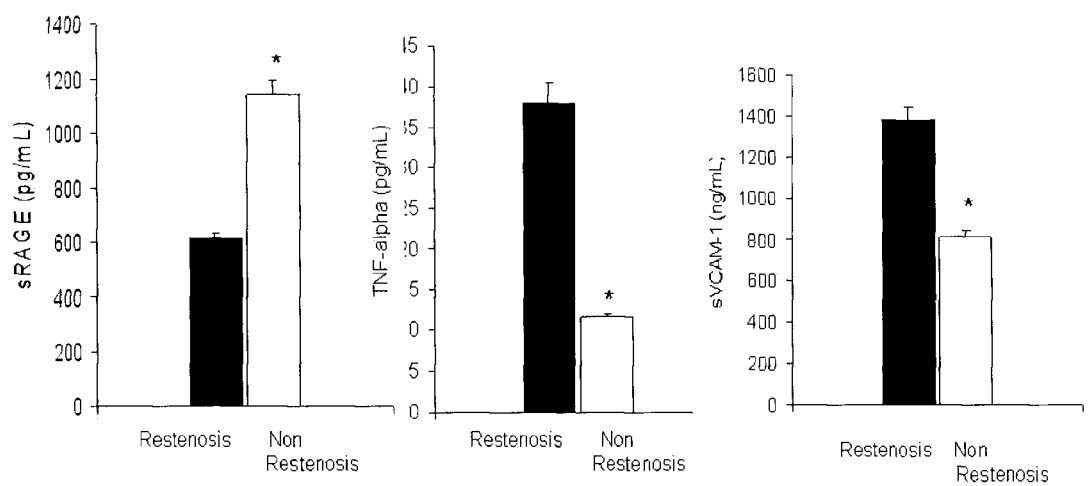
FIG. 6 depicts the pre-PCI levels of serum sRAGE, TNF-α and sVCAM-1 in NSTEMI patients with or without restenosis. Results are expressed as mean±SE. *p<0.05, restenosis vs. non-restenosis.
Figure 7:
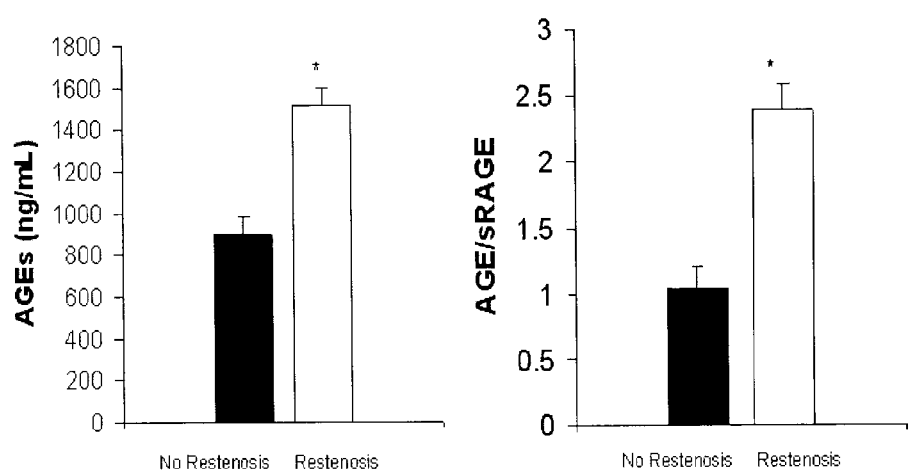
FIG. 7 depicts the pre-PCI levels of AGE and the ratios of AGE/sRAGE in patients with or without restenosis. Results are expressed as mean±SE. *p<0.05, restenosis vs. no restenosis.

The pre-PCI levels of serum sRAGE, TNF-α and sVCAM-1 in the restenosis and non-restenosis groups are summarized in FIG. 6; the pre-PCI levels of serum AGE and AGE/sRAGE in the restenosis and non-restenosis groups are summarized in FIG. 7.

Levels of sRAGE in the restenosis group were significantly lower compared to the non-restenosis group (626.0±26.0 vs. 1104.0±58.0 pg/ml). However the serum levels of TNF-α and sVCAM-1 were higher in the restenosis group than in the non-restenosis group (TNF-α, 34.0±2.9 vs. 11.63±0.62 pg/ml; sVCAM-1, 1290±89 vs. 827.6±43.3 ng/ml). The pre-PCI levels of serum AGE in patients with restenosis were significantly higher compared to those in patients without restenosis (1512.06±84.53 vs. 891.71±92.24 ng/ml). The pre-PCI ratio of AGE/sRAGE was 2.32 times higher in patients with restenosis compared to patients without restenosis (2.39±0.20 vs. 1.03±0.17).

These results indicate that the patients with restenosis had lower levels of pre-PCI sRAGE and higher levels of AGE, AGE/sRAGE, TNF-α and sVCAM-1 compared to patients without restenosis.

2. Post-PCI Serum Levels of sRAGE, TNF-α and sVCAM-1

Figure 8:
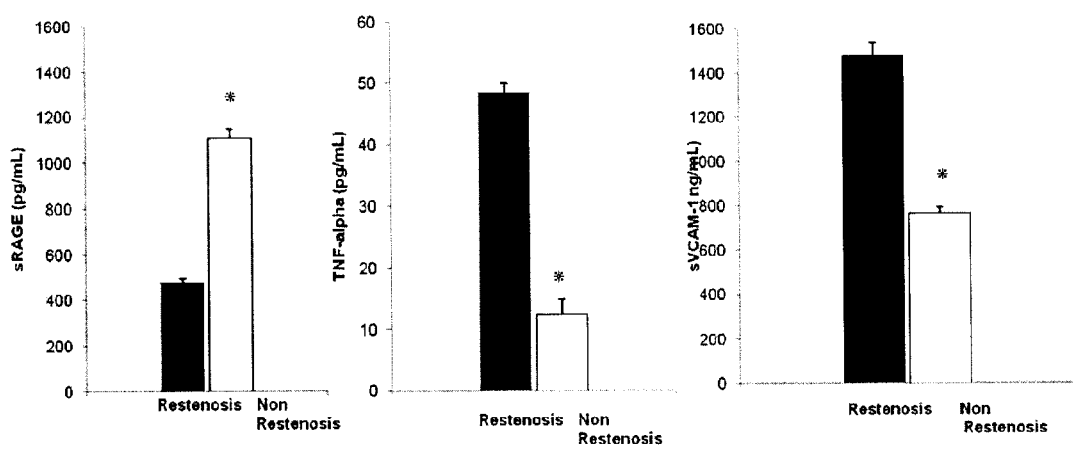
FIG. 8 depicts the post-PCI levels of serum sRAGE, TNF-α and sVCAM-1 in NSTEMI patients with or without restenosis. Results are expressed as mean±SE. *p<0.05, restenosis vs. non-restenosis.
Figure 9:
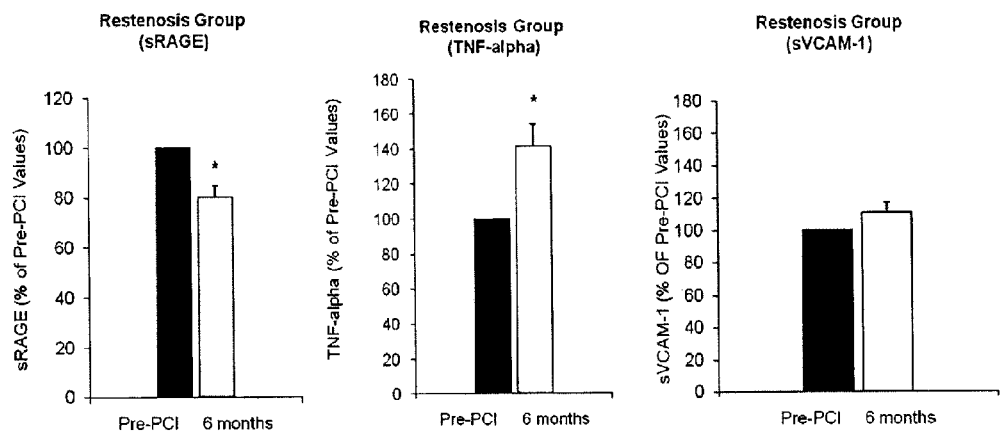
FIG. 9 depicts the pre- and post-PCI levels of serum sRAGE, TNF-α and sVCAM-1 in patients with restenosis. The results are expressed as mean±SE. *p<0.05, pre-PCI vs. six months post-PCI.

The post-PCI levels of sRAGE, TNF-α and sVCAM-1 in patients with or without restenosis are summarized in FIG. 8. The levels of sRAGE in patients with restenosis were significantly lower than those in patients without restenosis (477.0±18.6 vs. 1106.7±41.9 pg/ml). The levels of TNF-α and sVCAM-1 were higher, however, in patients with restenosis compared to patients without restenosis (TNF-α, 48.4±1.4 vs. 12.5±0.4 pg/ml; sVCAM-1, 1381.8±63.5 vs. 767.2±26.4 ng/ml). The post-PCI levels of serum sRAGE were lower, TNF-α were higher, and sVCAM-1 remained unaltered compared to the pre-PCI levels in patients with restenosis (FIG. 9). On the other hand, the pre- and post-PCI levels of serum sRAGE, TNF-α and sVCAM-1 were similar in patients without restenosis (data not shown).

These results indicate that the post-PCI levels of serum sRAGE are lower, and of sVCAM-1 and TNF-α are higher in patients with restenosis compared to patients without restenosis. These results also indicate that the post-PCI levels of sRAGE are lower, TNF-α higher, and sVCAM-1 unaltered compared to pre-PCI levels in patients who developed restenosis. Pre- and post-PCI levels of sRAGE, TNF-α and sVCAM-1 were similar in patients who did not develop restenosis.

3. Correlation of sRAGE to TNF-α and sVCAM-1

Figure 10:
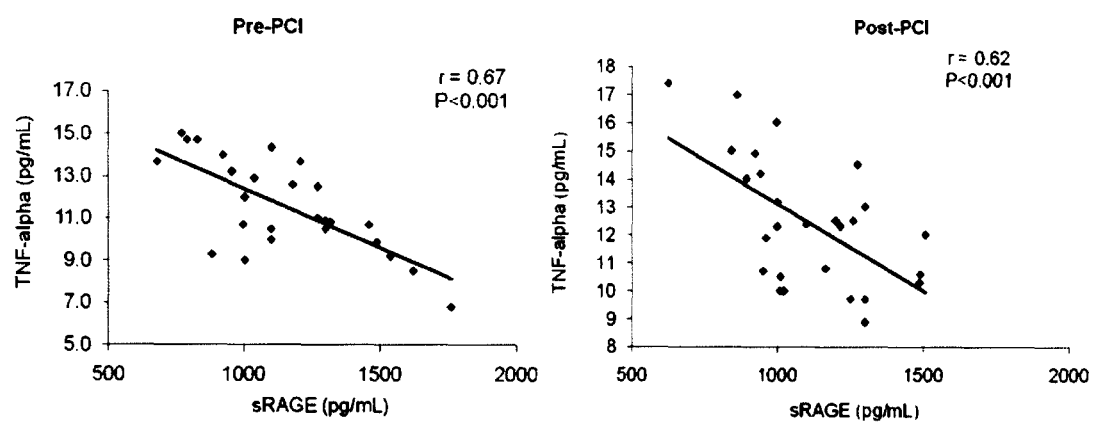
FIG. 10 depicts the correlation between pre-PCI levels or sRAGE and TNF-α, and between post-PCI levels of sRAGE and TNF-α in NSTEMI patients without restenosis.
Figure 11:
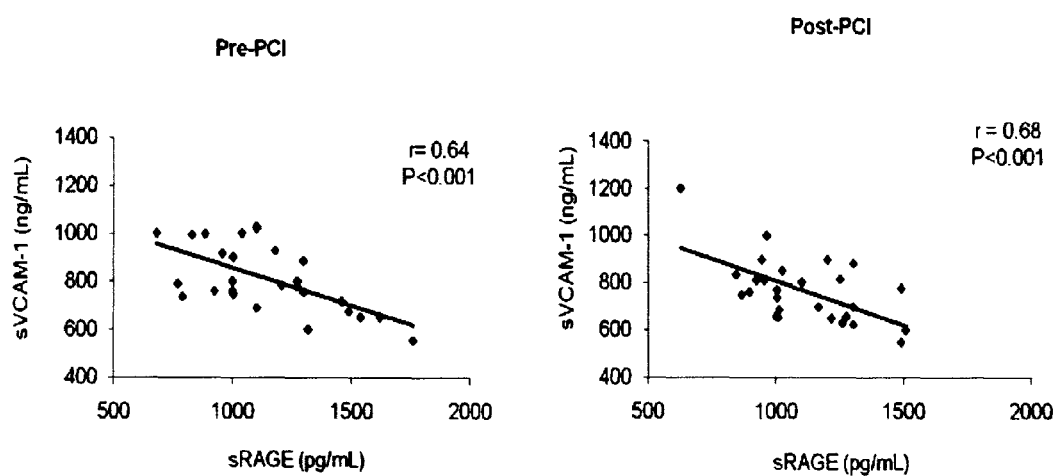
FIG. 11 depicts the correlation between pre-PCI levels of sRAGE and sVCAM-1, and between post-PCI levels of sRAGE and sVCAM-1 in NSTEMI patients without restenosis.

The correlation between pre- and post-PCI levels of serum sRAGE and TNF-α in patients who did not develop restenosis is shown in FIG. 10. The pre- and post-PCI levels of serum sRAGE negatively correlated with pre- and post-PCI levels of serum TNF-α in patients who did not develop restenosis. The pre- and post-PCI levels of serum sRAGE were negatively correlated with pre- and post-PCI levels of sVCAM-1 in patients who did not develop restenosis (FIG. 11). Similar relationships between the pre- and post-PCI levels of sRAGE and pre- and post-PCI levels of TNF-α and sVCAM-1 were observed in patients who developed post-PCI restenosis (data not shown). These correlations were significant.

These data indicate that serum levels of sRAGE are negatively correlated with serum levels of TNF-α and sVCAM-1, irrespective of pre- and post-PCI status or patients with or without restenosis.

4. Sensitivity, Specificity, Predictive Values and Accuracy of the sRAGE and AGE/sRAGE Tests in Identifying Patients Who Would Develop Post-PCI Restenosis The data for sensitivity, specificity, predictive values and accuracy of the pre-PCI serum sRAGE and AGE/sRAGE tests for diagnosis of post-PCI restenosis in ACS (NSTEMI) patients are shown in FIG. 13. Sensitivity refers to probability that a test will be positive in patients with disease. Specificity refers to probability that a test will be negative in individuals without disease. Positive predictive value (PPV) refers to probability that a patient will have disease given a positive test result. Negative Predictive Value (NPV) refers to probability that an individual will not have a disease given a negative rest result. Accuracy refers to probability of correctly identifying subjects. NSTEMI refers to Non-St-elevation myocardial infarction. The sensitivity and negative predictive values of the sRAGE test in identifying patients with post-PCI restenosis were 100%, while the specificity, positive predictive value and accuracy were 83%, 85% and 91%, respectively. The sensitivity, specificity, positive predictive value, negative predictive value and accuracy of the AGE/sRAGE test were 81%, 94%, 93%, 84% and 88%, respectively. In general, both tests have predictive value for post-PCI restenosis, however, the sRAGE test has greater sensitivity and negative predictive value than the AGE/sRAGE test in predicting post-PCI restenosis.

These results indicate that both sRAGE and AGE/sRAGE tests are predictors/biomarkers for post-PCI restenosis in ACS (NSTEMI) patients undergoing PCI procedures. The sRAGE test has greater sensitivity and negative predictive value compared to the AGE/sRAGE test.

Discussion

The results of this study show that patients with ACS have lower levels of sRAGE and higher levels of serum TNF-α and sVCAM-1 compared to control subjects. This study also demonstrated that ACS patients who developed restenosis following PCI had lower levels of serum sRAGE and higher levels of serum TNF-α and sVCAM-1 compared to those ACS patients who did not develop restenosis following PCI.

The question arises why subjects with low sRAGE develop ACS and develop restenosis following PCI. As shown in the results there is an inverse relationship between serum sRAGE and TNF-α, and between serum sRAGE and sVCAM-1. While not wishing to be bound by theory, the low sRAGE may induce development of atherosclerosis (stenosis) via an increase in the levels of serum TNF-α and sVCAM-1.

TNF-α is known to activate granulocytes to generate reactive oxygen species (ROS) (15-17). TNF-α also stimulates NADPH-oxidase in the endothelial cells to generate ROS (18, 19). ROS have been implicated in the development of hypercholesterolemic atherosclerosis (20-24). Reactive oxygen species increase the expression of adhesion molecules including VCAM-1 (25-29). Circulating concentrations of adhesion molecules are elevated in atherosclerosis (30). Adhesion molecules mediate monocyte adhesion to endothelial cells, and their transmigration to the vascular wall (31). The interaction and adhesion of monocytes to the endothelium have been recognized as important steps in the development and progression of atherosclerosis (32). Following their adhesion to the endothelial cell lining of the vessel walls, monocytes transmigrate to the intima, where they are transformed into activated macrophages, and accumulate lipids to become foam cells, a major component of fatty streaks (33).

Again, while not wishing to be bound by theory, decreases in the levels of sRAGE may allow more free RAGE to interact with AGEs. Interaction of AGEs with RAGE in smooth muscle cells (SMC) could lead to the secretion of transforming growth factor-$\beta$ (TGF-$\beta$), resulting in SMC migration and extracellular matrix formation, and hence modulation of atherosclerosis (34).

REFERENCES

1. Thorpe S R, Baynes J W. Maillard reaction products in tissue proteins: new products and new perspectives. Amino Acids 2003; 25:275-281.
2. Prasad K. Soluble receptor for advanced glycation end products (sRAGE) and cardiovascular disease. Int J Angiol. 2006; 15:57-68.
3. Huttunen H J, Kuja-Panula J, Sorci G, Agneletti A L, Donato R, Rauvala H. Coregulation of neurite outgrowth and cell survival by amphoterin and S100 proteins through receptor for advanced glycation end products (RAGE) activation. J Biol Chem. 2000; 275:40096-40105.
4. Hofmann M A, Drury S, Fu C, Qu W, Taguchi A, Lu Y, Avila C, Kambhan N, Bierhaus A, Neurath M F, Nawroth P, Slattery T, Beach D, McClary J, Nagashima M, Morser J, Stem D, Schmidt A M. RAGE mediates a novel proinflammatory axis: a central cell surface receptor for S100/calgranulin polypeptides. Cell. 1999; 97:889-901.
5. Neumann A, Schinzel R, Palm D, Riederer P, Münch G. High molecular weight hyaluronic acid inhibits advanced glycation endproduct-induced NF-kappaB activation and cytokine expression. FEBS Lett. 1999; 453:283-287.
6. Reznikov L L, Waksman J, Azam T, Kim S H, Bufler P, Niwa T, Werman A, Zhang X, Pischetsrieder M, Shaldon S, Dinarello C A. Effect of advanced glycation end products on endotoxin-induced TNF-alpha, IL-1beta and IL-8 in human peripheral blood mononuclear cells. Clin Nephrol. 2004; 61:324-336.
7. Rosca M G, Mustata T G, Kinter M T, Ozdemir A M, Kern T S, Szweda L I, Brownlee M, Monnier V M, Weiss M F. Glycation of mitochondrial proteins from diabetic rat kidney is associated with excess superoxide formation. Am J Physiol Renal Physiol. 2005; 289:F420-430.
8. Yonekura H, Yamamoto Y, Sakurai S, Petrova R G, Abedin M J, Li H, Yasui K, Takeuchi M, Makita Z, Takasawa S, Okamoto H, Watanabe T, Yamamoto H. Novel splice variants of the receptor for advanced glycation end-products expressed in human vascular endothelial cells and pericytes, and their putative roles in diabetes-induced vascular injury. Biochem J. 2003; 370:1097-1109.
9. Chavakis T, Bierhaus A, Al-Fakhri N, Schneider D, Witte S, Linn T, Nagashima M, Morser J, Arnold B, Preissner K T, Nawroth P P. The pattern recognition receptor (RAGE) is a counter receptor for leukocyte integrins: a novel pathway for inflammatory cell recruitment. J Exp Med. 2003; 198:1507-1515.
10. Kastrati A, Mehilli J, Dirschinger J, Pache J, Ulm K, Schühlen H, Seyfarth M, Schmitt C, Blasini R, Neumann F J, Schömig A. Restenosis after coronary placement of various stent types. Am J Cardiol. 2001; 87:34-39.
11. Zhou Z, Wang K, Penn M S, Marso S P, Lauer M A, Forudi F, Zhou X, Qu W, Lu Y, Stern D M, Schmidt A M, Lincoff A M, Topol E J. Receptor for AGE (RAGE) mediates neointimal formation in response to arterial injury. Circulation. 2003; 107:2238-2243.
12. Sakaguchi T, Yan S F, Yan S D, Belov D, Rong L L, Sousa M, Andrassy M, Marso S P, Duda S, Arnold B, Liliensiek B, Nawroth P P, Stern D M, Schmidt A M, Naka Y. Central role of RAGE-dependent neointimal expansion in arterial restenosis. J Clin Invest. 2003; 111:959-972.
13. Wendt T M, Bucciarelli L G, Ju Y, Qu W, Fan L, Tsai M, Ferran L J, Stern D M, Schmidt A M. Accelerated atherosclerosis and vascular inflammation develop in apoE null mice with type 2 diabetes. Circulation. 2000; 102:11-231 (Abstract).
14. Glas A S, Lijmer J G, Prins M H, Bonsel G J, Bossuyt P M M. The diagnostic odds ratio: a single indicator of test performance. J Clin Epidemiol. 2003; 56:1129-1135.
15. Braquet P, Hosford D, Braquet M, Bourgain R, Bussolino F. Role of cytokines and platelet-activating factor in microvascular immune injury. Int Arch Allergy Appl Immunol. 1989; 88:88-100.
16. Wang Q, Doerschuk C M, Mizgerd J P. Neutrophils in innate immunity. Semin Respir Crit Care Med. 2004; 25:33-41.
17. Yuo A, Kitagawa S, Kasahara T, Matsushima K, Saito M, Takaku F. Stimulation and priming of human neutrophils by interleukin-8: cooperation with tumor necrosis factor and colony-stimulating factors. Blood 1991; 78:2708-2714.
18. Gertzberg N, Neumann P, Rizzo V, Johnson A. NAD(P)H oxidase mediates the endothelial barrier dysfunction induced by TNF-alpha. Am J Physiol Lung Cell Mol Physiol. 2004; 286:L37-48.
19. Nwariaku F E, Liu Z, Zhu X, Nahari D, Ingle C, Wu R F, Gu Y, Sarosi G, Terada L S. NADPH oxidase mediates vascular endothelial cadherin phosphorylation and endothelial dysfunction. Blood. 2004; 104:3214-3220.
20. Prasad K, Kalra J. Oxygen free radicals and hypercholesterolemic atherosclerosis: effect of vitamin E. Am Heart J. 1993; 125:958-973.
21. Steinberg D. Antioxidants in the prevention of human atherosclerosis. Circulation. 1992; 85:2337-2344.
22. Prasad K. Reduction of serum cholesterol and hypercholesterolemic atherosclerosis in rabbits by secoisolariciresinol diglucoside isolated from flaxseed. Circulation. 1999; 99:1355-1362.
23. Prasad K. Hypocholesterolemic and antiatherosclerotic effect of flax lignan complex isolated from flaxseed. Atherosclerosis. 2005; 179:269-275.
24. Prasad K, Lee P. Suppression of hypercholesterolemic atherosclerosis by pentoxifylline and its mechanism. Atherosclerosis. 2007; 192:313-322.
25. Chiu J J, Wung B S, Shyy J Y, Hsieh H J, Wang D L. Reactive oxygen species are involved in shear stress-induced intercellular adhesion molecule-1 expression in endothelial cells. Arterioscler Thromb Vasc Biol. 1997; 17:3570-3577.
26. Kaneko M, Hayashi J, Saito I, Miyasaka N. Probucol downregulates E-selectin expression on cultured human vascular endothelial cells. Arterioscler Thromb Vasc Biol. 1996; 16:1047-1051.
27. Faruqi R, de la Motte C, DiCorleto P E. Alpha-tocopherol inhibits agonist-induced monocytic cell adhesion to cultured human endothelial cells. J Clin Invest. 1994; 94:592-600.
28. Devaraj S, Li D, Jialal I. The effects of alpha tocopherol supplementation on monocyte function. Decreased lipid oxidation, interleukin 1 beta secretion, and monocyte adhesion to endothelium. J Clin Invest. 1996; 98:756-763.

29. Martin A, Foxall T, Blumberg J B, Meydani M. Vitamin E inhibits low-density lipoprotein-induced adhesion of monocytes to human aortic endothelial cells in vitro. Arterioscler Thromb Vasc Biol. 1997; 17:429-436.
30. Gearing A J, Newman W. Circulating adhesion molecules in disease. Immunol Today. 1993; 14:506-512.
31. Gimbrone M A Jr. Vascular endothelium: an integrator of pathophysiologic stimuli in atherosclerosis. Am J Cardiol. 1995; 75:67B-70B.
32. Libby P, Hansson G K. Involvement of the immune system in human atherogenesis: current knowledge and unanswered questions. Lab Invest. 1991; 64:5-15.
33. Ross R. Rous-Whipple Award Lecture. Atherosclerosis: a defense mechanism gone awry. Am J Pathol. 1993; 143: 987-1002.
34. Higashi T, Sano H, Saishoji T, Ikeda K, Jinnouchi Y, Kankazi T, Morisaki N, Rauvala H, Shichiri M, Horiuchi S. The receptor for advanced glycation end products mediates the chemotaxis of rabbit smooth muscle cells. Diabetes. 1997; 46:463-472.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A method comprising:
   a) obtaining a serum sample from a subject;
   b) processing said sample;
   c) performing a binding assay comprising contacting the processed sample with an antibody to sRAGE (soluble receptor for advanced glycation endproducts) to form a complex between the antibody and sRAGE present in the processed sample; said binding assay generating at least one assay result indicative of said complex; and
   d) administering a treatment of acute coronary syndrome (ACS) to said subject when the amount of sRAGE in said sample is low compared to a control.

2. The method of claim 1, wherein instrumentation having a detector set to detect the complex formed between said antibody and said sRAGE in said sample is used to determine an amount of complex in the sample.

3. The method of claim 2, wherein said instrumentation is a spectrophotometer, spectrofluorometer, optical device or electrochemical device.

4. The method of claim 1, wherein said ACS is NSTEMI (Non-ST-elevation myocardial infarction), STEMI (ST-elevation myocardial infarction) or acute angina.

5. A method comprising:
   a) obtaining a serum sample from a subject with ACS;
   b) processing said sample;
   c) performing a binding assay comprising contacting the processed sample with an antibody to a biomarker within said sample to form a complex between the antibody and said biomarker; said binding assay generating at least one assay result indicative of said complex; and
   d) administering a treatment of PCI (percutaneous coronary intervention) to said subject,
   wherein the biomarker is sRAGE and the amount of sRAGE in said sample is low compared to a control.

6. The method of claim 5, wherein instrumentation having a detector set to detect the complex formed between said antibody and the biomarker in said sample is used to determine an amount of complex in the sample.

7. The method of claim 6, wherein said instrumentation is a spectrophotometer, spectrofluorometer, optical device or electrochemical device.

8. The method of claim 5, wherein said subject is a human.

9. The method of claim 5, wherein said ACS is NSTEMI (Non-ST-elevation myocardial infarction), STEMI (ST-elevation myocardial infarction) or acute angina.

10. A method comprising:
    a) obtaining a serum sample from a subject with ACS;
    b) processing said sample;
    c) performing a first binding assay comprising contacting a first portion of said processed sample with an antibody to sRAGE (soluble receptor for advanced glycation endproducts) to form a first complex between the antibody and sRAGE present in the processed sample, said first binding assay generating at least one assay result indicative of said first complex;
    d) performing a second binding assay comprising contacting a second portion of the processed sample with an antibody to AGE (advanced glycation endproduct) to form a second complex between the antibody and AGE present in the sample, said second binding assay generating at least one assay result indicative of said second complex;
    e) administering a treatment for post-PCI (post-percutaneous coronary intervention) restenosis when the ratio of AGE/sRAGE in said sample is high compared to a control.

11. The method of claim 10, wherein instrumentation having a detector set to detect said first complex and said second complex is used to determine an amount of each said first complex and said second complex in the sample.

12. The method of claim 11, wherein said instrumentation is a spectrophotometer, spectrofluorometer, optical device or electrochemical device.

13. The method claim 10, wherein said subject is a human.

14. The method claim 10, wherein said ACS is NSTEMI (Non-ST-elevation myocardial infarction), STEMI (ST-elevation myocardial infarction) or acute angina.

* * * * *